United States Patent
Ramiya et al.

(10) Patent No.: US 7,202,080 B2
(45) Date of Patent: Apr. 10, 2007

(54) METHOD FOR TRANSDIFFERENTIATION OF NON-PANCREATIC STEM CELLS TO THE PANCREATIC DIFFERENTIATION PATHWAY

(75) Inventors: Vijaykumar Ramiya, Gainesville, FL (US); Amy Clark, Gainesville, FL (US)

(73) Assignee: Ixion Biotechnology, Inc., Alachua, FL (US)

( * ) Notice: Subject to any disclaimer, the term of this patent is extended or adjusted under 35 U.S.C. 154(b) by 8 days.

(21) Appl. No.: 10/113,118

(22) Filed: Mar. 29, 2002

(65) Prior Publication Data

US 2002/0182728 A1 Dec. 5, 2002

Related U.S. Application Data

(60) Provisional application No. 60/279,922, filed on Mar. 29, 2001.

(51) Int. Cl.
*C12N 5/00* (2006.01)
*C12N 5/02* (2006.01)
*A01N 63/00* (2006.01)
*A01N 65/00* (2006.01)

(52) U.S. Cl. .................. 435/325; 435/405; 435/375; 424/93.1

(58) Field of Classification Search .............. 435/325, 435/334, 335, 336, 372, 375; 624/93.1
See application file for complete search history.

(56) References Cited

U.S. PATENT DOCUMENTS

| | | | |
|---|---|---|---|
| 4,439,521 A | 3/1984 | Archer et al. | |
| 4,714,680 A | 12/1987 | Civin | |
| 5,061,620 A | 10/1991 | Tsukamoto et al. | |
| 5,447,863 A | 9/1995 | Langley | |
| 5,486,359 A | 1/1996 | Caplan et al. | |
| 5,589,376 A | 12/1996 | Anderson et al. | |
| 5,750,397 A | 5/1998 | Tsukamoto et al. | |
| 5,834,308 A | 11/1998 | Peck et al. | |
| 5,840,580 A | 11/1998 | Terstappen et al. | |
| 5,843,780 A | 12/1998 | Thomson | |
| 6,001,647 A | 12/1999 | Peck et al. | |
| 6,200,806 B1 | 3/2001 | Thomson | |
| 6,242,666 B1 | 6/2001 | Sarvetnick et al. | |
| 6,703,017 B1 | 3/2004 | Peck et al. | |
| 2001/0024824 A1* | 9/2001 | Moss et al. | 435/366 |
| 2001/0046489 A1* | 11/2001 | Habener et al. | 424/93.21 |
| 2005/0053588 A1 | 3/2005 | Yin | |

FOREIGN PATENT DOCUMENTS

| | | |
|---|---|---|
| EP | 0 363 125 | 10/1998 |
| WO | WO 86/01530 | 3/1986 |
| WO | WO 93/00441 | 1/1993 |
| WO | WO 94/23572 | 10/1994 |
| WO | WO9529988 | 11/1995 |
| WO | WO 96/15230 | 5/1996 |
| WO | WO9715310 | 5/1997 |
| WO | WO 00/53795 | 9/2000 |
| WO | WO00/72885 | 12/2000 |
| WO | WO 01/00650 | 1/2001 |
| WO | WO 01/11011 | 2/2001 |
| WO | WO0123528 | 4/2001 |
| WO | WO 04/087885 | 10/2004 |

OTHER PUBLICATIONS

Ho et al .Journal of Leukocyte Biology 73:547-555, 2003.*
Herzog et al. Blood 102:3483-3493, 2003.*
Hess et al Nature Biotechnology 21:763-770, 2003.*
Choi et al. Diabetologia 46:1366-1374, 2003.*
Ferber et al. (2002) Nat. Med. 6(5):568-572.
Yang et al. (2002) PNAS 99(12):8078-8083.
Alison et al. (2000) Nature 406: 257.
Bonner-Weir et al. (2000) Proc. Natl. Acad. Sci. USA 97:7999-8004.
Civin et al. (1990) Prog. Clin. Biol. Res. 333:387-401.
Dexter et al. (1990) Ciba Found. Symp. 148:76-86.
Goodell et al. (2001) Ann. NY Acad. Sci. 938:18.
Gussoni et al. (1999) Nature 401:390-394.
Heyworth et al. (1997) In: Stem Cells, Academic Press Ltd., pp. 243-441.
Lemischka (1999) Proc. Natl. Acad. Sci. USA 96:14193-14195.
Ramiya et al. (2000) Nat. Med. 6:278-282.
Pittenger et al. (1999) Science 284:143-146.
Yin et al. (2002) Hepatology 35(2):315-324.
Yin et al. (1999) J. Hepatol. 31:497-507.
Yin et al. (2001) FASEB J. Late-Breaking Abstracts:49 (LB267).
Yin et al. (2001) PAACR 42:354.
Song et al. (1999) Gastroenterology 117:1416-1426.
Beattie et al. (Sep. 1986) Diabetes 45:1223-1228.
Horb et al. (Jan. 2003) Current Biology 13:105-115.
Suzuki et al (Jan. 2002) The Journal of Cell Biology 156(1):173-184.

(Continued)

*Primary Examiner*—Joseph Woitach
(74) *Attorney, Agent, or Firm*—Swanson & Bratschun L.L.C.

(57) ABSTRACT

The subject invention comprises culture methods for transdifferentiation of non-pancreatic stem cells to the pancreatic differentiation pathway. It also concerns the endocrine hormones that can be produced by such cultures, and the use of the transdifferentiated cells in the treatment of pancreatic diseases.

6 Claims, 3 Drawing Sheets

OTHER PUBLICATIONS

Halkin et al. (Aug. 2000) Diabetolgia 43(1):A58.
Lumelsky et al. (May 2001) Science 292 (5520):1389-1394.
Hayek et al (Dec. 1995) Diabetes 44(12);1458-1460.
Peshavaria et al. (1997) Pancreatic Growth and Regeneration, pp. 96-107.
Kahn (2000) Nature Med. 6(5):505-506.
Soria Bernat et al. (2000) Diabetes 49(2):157-162.
Gazdar et al. (1980) Proc. Natl. Acad. Sci. 77(6):3519-3525.
McEvoy et al. (1982) Endocrinol. 111(5):1568-1575.
Korsgren et al. (1993) J. Med. Sci. 98(1):39-52.
Schuldiner et al. (2000) "Effects of eight growth factors on the differentiation of cells derived from human embryonic stem cells", PNAS usa 97:11307.
Terada et al. (2002) "Bone marrow cells adopt the phenotype of other cells by spontaneous cell fusion", Nature 416:542.
Wells et al. (2002) "Is transdifferentiation in trouble", J. Cell Biol. 157:15.

* cited by examiner

Treatment of CD34+ Stem Cells With Factors

14 Days
- ISL-1
- PAX 6
- PAX 4
- CK19
- CD34

45 Days
- G3PDH
- CK19
- Insulin

Human Bone Marrow-Derived CD34+ Stem Cells

Basal Medium

Basal Medium+Factors

Mesenchymal Stem Cells

Basal Medium

Figure 3

METHOD FOR TRANSDIFFERENTIATION OF NON-PANCREATIC STEM CELLS TO THE PANCREATIC DIFFERENTIATION PATHWAY

RELATEDNESS OF THE APPLICATION

This application claims the benefit of priority to U.S. Ser. No. 60/279,922, filed Mar. 29, 2001.

FIELD OF THE INVENTION

The subject invention relates to culture methods for the transdifferentiation of non-pancreatic stem cells, and in particular hematopoietic stem cells and mesenchymal stem cells, to the pancreatic differentiation pathway. It also concerns the use of transdifferentiated cells to treat pancreatic disorders.

BACKGROUND OF THE INVENTION

Diabetes is a major public health problem. In the United States, sixteen million persons have diabetes (American Diabetes Association, Professional Section Quarterly, Summer 1998). Ocular complications of diabetes are the leading cause of new cases of legal blindness in people ages 20 to 74 in the United States. The risk for lower extremity amputation is 15 times greater in individuals with diabetes than in individuals without it. Kidney disease is a frequent and serious complication of diabetes. Approximately 30 percent of all new patients in the United States being treated for end-stage renal disease have diabetes. Individuals with diabetes are also at increased risk for periodontal disease. Periodontal infections advance rapidly and lead not only to loss of teeth but also to compromised metabolic function. Women with diabetes risk serious complications of pregnancy. Current statistics suggest that the mortality rates for infants of mothers with diabetes is approximately 7 percent.

Clearly, the economic burden of diabetes is enormous. Each year, patients with diabetes or its complications spend 24 million patient-days in hospitals. Diabetes is our nation's most expensive disease with an estimated total annual cost of $98 billion; however, the full economic impact of this disease is even greater because additional medical expenses often are attributed to the specific complications of diabetes rather than to diabetes itself.

Diabetes is a chronic, complex metabolic disease that results in the inability of the body to properly maintain and use carbohydrates, fats, and proteins. It results from the interaction of various hereditary and environmental factors and is characterized by high blood glucose levels caused by a deficiency in insulin production or an impairment of its utilization. Most cases of diabetes fall into two clinical types: Type I, or juvenile-onset, and Type II, or adult-onset. Type I diabetes is often referred to as Insulin Dependent Diabetes, or IDD. Each type has a different prognosis, treatment, and cause.

Approximately 5 to 10 percent of diabetes patients have IDD. IDD is characterized by a partial or complete inability to produce insulin usually due to destruction of the insulin-producing cells of the pancreatic islets of Langerhans. Patients with IDD would die without daily insulin injections to control their disease. Additionally, a fraction of Type II diabetics are insulin dependent and require insulin injections to improve their insulin resistance. Both Type I and insulin-dependent Type II diabetics can benefit from improvements in insulin administration, such as those described herein.

Few advancements in resolving the pathogenesis of diabetes were made until the mid-1970s when evidence began to accumulate to suggest that Type I IDD had an autoimmune etiopathogenesis. It is now generally accepted that IDD results from a progressive autoimmune response which selectively destroys the insulin-producing cells of the pancreatic Islets of Langerhans in individuals who are genetically predisposed. Autoimmunity to the cell in IDD involves both humoral (Baekkeskov et al. (1982) Nature 298:167; Baekkeskov et al. (1990) Nature 347:151; Reddy et al. (1988) Diabetologia 31:322; Pontesilli et al. (1987) Clin. Exp. Immunol. 70:84) and cell-mediated (Reddy et al. (1988); Pontesilli et al. (1987); Wang et al. (1987) Diabetes 36:535) immune mechanisms. Humoral immunity is characterized by the appearance of autoantibodies to cell membranes (anti-69 kD and islet-cell surface autoantibodies), cell contents (anti-carboxypeptidase $A_1$, anti-64 kD and/or anti-GAD autoantibody), and/or cell secretory products (anti-insulin). While serum does not transfer IDD, anti-cell autoantibody occurs at a very early age, raising the question of an environmental trigger, possibly involving antigenic mimicry. The presence of cell-mediated immunological reactivity in the natural course of IDD is evidenced by an inflammatory lesion within the pancreatic islets, termed insulitis. Insulitis, in which inflammatory/immune cell infiltrates are clearly visible by histology, has been shown to be comprised of numerous cell types, including T and B lymphocytes, monocytes and natural killer cells (Signore et al. (1989) Diabetologia 32:282; and Jarpe et al. (1991) Regional Immunol. 3:305). Adoptive transfer experiments using the NOD (non-obese diabetic) mouse as a model of human IDD have firmly established a primary role for auto-aggressive T lymphocytes in the pathogenesis of IDD (Bendelac, et al. (1987) J. Exp. Med. 166:823; Miller et al. (1988) J. Immunol. 140:52; Hanafusa et al. (1988) Diabetes 37:204; and Bendelac et al. (1988) J. Immunol. 141:2625). Unfortunately, the mechanisms underlying destruction of the pancreatic cells remain unknown.

The mammalian pancreas controls nutrient resorption and glucose metabolism through its major components, the ductal cells, acinar cells and endocrine cells. The endocrine cells include insulin-produce β cells. Despite the fact that all three components of the pancreas differ in functionality, they are all of the same origin, the primitive gut endoderm. During early gestation (28 days in humans) evaginations of the embryonal foregut form the ventral and dorsal buds of the pancreas. The two buds arise opposite to each other while the gut is still surrounded by primitive mesenchyme. After rotation of the stomach and duodenum, the ventral anlage moves around and fuses with the dorsal bud. The ventral bud forms the posterior part of the pancreatic head including the ulcinate process, while the dorsal bud forms the remainder of the organ. In the enlarging epithelial buds, a treelike ductal system develops which eventually gives rise to endocrine and acinar cells (Peters et al. (2000) Virchows Arch. 436:527–538). It is believed that the "protodifferentiated" epithelial cells which reside in the ducts also share the features of ductal cells (Pictet et al. (1972) Development of the embryonic endocrine pancreas, In: Geiger S R (ed.) Handbook of Physiology, sect 7: Endocrinology, Waverley Press, Baltimore, pp25–66). These and more recent observations suggest that the pancreatic duct cells harbor the stem cells, which under appropriate stimuli, can give rise to acinar and endocrine cells (Ramiya V. et al. (2000) Nat. Med. 6:278–282; Bonner-Weir et al. (2000) Proc. Natl. Acad. Sci. USA 97:7999–8004). The pancreatic ductal progenitor stem cells have been shown to express tyrosine hydroxylase (Teitelman et al. (1993) Development 118:1031–1039), glucose transporter (GLUT-2) (Pang et al. (1994) Proc. Natl. Acad. Sci. USA 91:9559–9563), cytokeratins (Bouwens et al. (1994) Diabetes 43:1279–1283), Pdx-1 (Jonsson et al. (1994) Nature 371:606–609), high-affinity nerve growth factor TrkA (Kanaka-Gantenbein et al. (1995) Endocrinology 136:3154–3162), Isl-1 (Ahlgren et al. (1997) Nature 385:257–60), and ngn-3 (Gradwohl et al. (2000) Proc. Natl. Acad. Sci. USA 97:1607–1611). In the human fetal pancreas, proliferation is mainly found in the ductal cell compartment, followed in frequency by endocrine cells, which are synaptophysin positive but hormone negative, and finally, insulin or glucagon positive cells. In addition, it was noted that all epithelial cells, including endocrine cells, express cytokeratin 19 from 12–16 gestation weeks. The cytokeratin disappears later from the endocrine cells (Bouwens et al. (1997) Diabetologia 40:398–404).

For IDD patients, regular insulin injections do not maintain blood glucose near normal levels at all times and consequently patients develop secondary complications. While pancreatic and islet transplantations can consistently establish a euglycemic state and significantly reduce long-term complications, availability of the grafts is severely limited. Xenotransplants, on the other hand, pose a potentially serious threat of xenosis (transfer of animal infections to humans) with attendant regulatory problems and delays. Thus, there is an urgency to develop a pancreatic endocrine replacement therapy for Type 1 diabetic patients that would supply a sufficient number of functional human islets or their equivalents on demand.

One response to this need has been to develop in vitro culture methods for pancreatic differentiated cells or tumor cells (e.g., Gazdar et al. (1980) Proc. Natl. Acad. Sci. 77(6):3519–3525; Brothers, A., WO 93/00441; Korsgren et al. (1993) J. Med. Sci. 98(1):39–52; Nielson, J., WO 86/01530; McEvoy et al. (1982) Endocrinol. 111(5):1568–1575; Zayas et al., EP 0 363 125; and Coon et al., WO 94/23572). Such culture methods could be used to generate endocrine hormones or, in some instances, furnish cells for transplantation.

Another response has been to identify and culture pancreatic stem cells which can give rise to islet progenitor cells (IPCs) and IPC-derived islets (IdIs) or islet-like structures (see U.S. Ser. No. 09/406,253, filed Sep. 27, 1999, and Peck et al., WO 01/23528). The advantages of this method include the long-term propagation of the stem cells and the use of the stem cells and their progeny for implantation into patients, wherein they proliferate to form a pancreas-like structure that can restore euglycemia.

Notwithstanding the foregoing, there remains a need to develop additional pancreatic endocrine replacement therapies. The subject invention concerns the use of non-pancreatic stem cells in the development of therapies for IDD. Specifically, non-pancreatic stem cells are transdifferentiated to the pancreatic lineage.

A stem cell is a cell that has the capacity to both self-renew and to generate differentiated progeny. Two stem cells that are already in clinical use are hematopoietic stem cells (HSCs) and mesenchymal stem cells (MSCs). The mammalian hematopoietic system produces at least eight distinct lineages of mature blood cells in a continuous manner throughout adult life. These lineages include red blood cells, monocytic, granulocytic, basophilic, myeloid cells, the T and B cells and platelets. In this sense, hematopoiesis may resemble other developmental systems such as small intestine, epidermis, and hair follicle of the skin as well as the male germ cells. Other tissue types such as the liver, central nervous system and skeletal muscles seem to replenish more slowly, or in response to injury (Lemischka et al. (1986) Cell 45:917–927). Complex quantitative analyses of HSCs, in some cases, demonstrated that a single transplantable stem cell is both necessary and sufficient to transfer an intact, normal hematopoietic system to a recipient host (Jordan et al. (1990) Genes Dev. 4:220–232; and Smith L. et al. (1991) Proc. Natl. Acad. Sci. 88:2788–2792).

The proliferation and development of HSCs in vivo is promoted by contact with bone marrow stromal cells and the surrounding extracellular matrix. While there is some ability of soluble cytokines or growth factors to promote survival and proliferation of stem cells and their progeny in the absence of stromal cell matrix, the primitive HSCs can only be maintained, in the long term, when co-cultured with the appropriate stromal cell environment (Dexter et al. (1990) Ciba Found. Symp. 148:76–86). The characterization of CD34 antigen on HSCs, expressed only by 0.5–5% of human bone marrow cells, has enabled the purification of HSCs in commercial quantities. CD34 is not expressed on more mature counterparts (Civin et al. (1990) Prog. Clin. Biol. Res. 333:387–401). Using the long term bone marrow culture system, it has been established that CD34+ HSCs can survive in vitro and differentiate when allowed to grow in contact with bone marrow derived stromal cells, which produce a plethora of factors including M-CSF, GM-CSF, G-CSF, IL-1, IL-6, IL-7, TGF-beta, LIF, SCF (Heyworth et al. (1997) In: Stem Cells, Academic Press Ltd., pp243–441).

Both HSCs and MHCs have been suggested to share common bone marrow precursors that express CD34 antigen. Accordingly, CD50– and CD34+ cells give rise to MSCs, while CD50+ CD34+ cells give rise to HSCs. Also, circulating cells include fibroblast-like MSCs (also called fibrocytes) along with HSCs. The MSCs can differentiated into osteocytes, adipocytes and chondrocytes in vitro when appropriate growth factors are provided (Pittenger et al. (1999) Science 284:143–146).

Although less extensive, other studies have identified candidate stem cells from a number of other tissues (Reynolds et al. (1992) Science 255:1707–1710; Johansson et al. (1999) Cell 96:25–34; Potten et al., Int. J. Exp. Pathol. 78:219–243; Watt F (1998) Philos. Trans. R. Soc. London B 353:831–837; Alison M (1998) Curr. Opin. Cell Biol. 10:710–715; and Ramiya V. et al. (2000) Nat. Med. 6:278–282).

Recent progress in stem cell biology puts the traditional view that a cell's fate is sealed when it becomes part of endoderm, mesoderm, or ectoderm, the primary germ layers of the embryo, in paradox. More specifically, the assumption that the undifferentiated stem cell state as defined by the ability of stem cell to produce mature cell populations is limited to the range of cell types characteristic of each individual tissue (by implication, any given somatic stem cell is physically resident within its appropriate tissue) has been called into question (Lemischka I. (1999) Proc. Natl. Acad. Sci. USA 96:14193–14195). For instance, after transplantation into irradiated hosts, genetically labeled neural stem cells were found to produce a variety of blood cell types including myeloid and lymphoid cells as well as early hematopoietic cells (Bjornson et al. (1999) Science 283: 534–537). The muscle tissue has been shown to contain a population of stem cells with several characteristics of bone marrow-derived HSCs, including high efflux of the fluourescent dye Hoechst 33342 and expression of the stem cell antigens Sca-1 and c-Kit but not CD45. These stem cells have been suggested to be identical to muscle satellite cells, some of which lack myogenic regulators and which are capable of responding to hematopoietic signals (Jackson et al. (1999) Proc. Natl. Acad. Sci. USA 96:14482–14486). A similar observation has been made by another group who also demonstrated the muscle differentiation potential of a subset of bone marrow-derived stem cells (Gussoni et al. (1999) Nature 401:390–394). A possibility of HSCs mobilizing during liver failure to increase the regenerative capacity of the liver, though to a lesser extent, has been documented (Alison et al. (2000) Nature 406: 257). These observations invite speculation that the functional plasticity of somatic tissue derived stem cells may be greater than expected.

HSCs and MSCs are presently routinely used in the clinical setting and are commercially available. They can be purified from the peripheral blood or bone marrow using commercially available technology. Obtaining pancreatic endocrine tissue or hormones from HSCs or MSCs that have committed to the pancreatic differentiation pathway would be very useful in advancing the treatment of diabetes.

SUMMARY OF THE INVENTION

The subject invention concerns a method of directing or transdifferentiating mammalian non-pancreatic stem cells to enter the pancreatic differentiation pathway by culturing said stem cells in a medium under conditions that permit the expression of pancreatic differentiation markers. The medium used in the method can be any suitable medium, but in a preferred embodiment, comprises Dulbecco's Minimal Essential Medium (DMEM) with high glucose and sodium pyruvate, bovine serum albumin (BSA), 2-mercaptoethanol, fetal calf serum (FCS), penicillin and streptomycin (Pen-Strep), and insulin, transferrin and selenium (ITS) for at least about 10–14 days. Preferably, the concentrations of the medium components are as indicated in Table 1A. The subject method results in expression of any or all of the following pancreatic markers: Pdx-1, Isl-1, Pax-4, Pax-6, Glut-2, CK-19 and insulin.

The medium may further contain an effective combination and effective concentrations of suitable growth factors, including those selected from the group consisting of stem cell factor (SCF), glucagon-like peptide-1 (GLP-1), activin A, betacellulin, hepatocyte growth factor (HGF), epidermal growth factor (EGF), keratinocyte growth factor (KGF), prolactin (PRL), nerve growth factor (NGF), transforming growth factor-α (TGF-α), gastrin, and conditioned medium of a cell line selected from the group consisting of Capan-1, ARIP and AR42J. Preferably, the added growth factors include each of these factors in the concentrations indicated in Table 1B. To enhance commitment to the pancreatic pathway, LIF (leukocyte inhibiting factor, which inhibits HSC differentiation), and IL-3 and IL-7 (which induce HSC commitment to lymphoid and erythroid lineages) are omitted from the Table 1B factors.

The non-pancreatic stem cells can be any stem cell other than the pancreatic stem or progenitor cells, but are typically HSCs or MSCs. The HSCs are CD34+, and the MSCs are CD105+, CD166+, CD29+ and CD44+. HSCs can be obtained from peripheral blood or from bone marrow. MSCs can also be obtained from bone marrow. The stem cells may be human or those of any other mammal.

The subject invention also comprises a method of producing an endocrine hormone by culturing stem cells in the medium with added factors as described above, whereby an endocrine hormone is produced and optionally recovered. The subject invention also encompasses the endocrine hormones produced by this method.

In another embodiment, the subject invention is directed to a method of treating a mammal with a pancreatic disorder, by culturing stem cells as described herein whereby the cells enter the pancreatic differentiation pathway, and using a product of the culture method to treat the mammal. In one embodiment, the pancreatic disorder is insulin-dependent diabetes (IDD).

In one case, the culture product that is administered to the mammal is one or more pancreatic endocrine hormones. The culture product may also be the transdifferentiated HSCs and MSCs, which may be implanted in the mammal. Typical locations for implantations of such cells are liver, pancreatic or kidney tissue, or in a subcutaneous pocket. It is preferred that, where implantation is contemplated, the non-pancreatic stem cells originate from the same species, and more preferably, the same individual that is to be treated so as to minimize the potential for immune rejection. The stem cells and the individual to be treated may be human or any other mammal.

Where there is some question of immune rejection, the cells or aggregates of cells that are to be implanted in the individual can be encapsulated in a hormone permeable capsule. Such capsule permits the flow of hormones from the implanted material, and the influx of oxygen and other nutrients, while inhibiting the influx of immune cells and antibodies.

Additionally, the transdifferentiated cells can be protected from immune rejection by modifying cell expression of selected proteins. For example, the cultured transdifferentiated cells can be transformed to express a protein or peptide which will inhibit or prevent the destructive immune process. Other useful proteins or peptides may be expressed. In addition, expression of autoantigens specific to the IDD process, such as GAD, 64 kD islet cell surface antigens (see Payton et al. (1995) J. Clin. Invest. 96:1506–1511), to the extent they may be expressed by the transdifferentiated cells, or any other markers identified on the transdifferentiated cells, can be eliminated by standard gene knock-out or selection procedures to produce transdifferentiated cells which are not or are less susceptible to autoimmune attack. Methods for producing such mutant or knock out cells are well known in the art and include, for example, homologous recombination methods disclosed in U.S. Pat. No. 5,286,632; U.S. Pat. No. 5,320,962; U.S. Pat. No. 5,342,761; and in WO 90/11354; WO 92/03917; WO 93/04169; WO 95/17911, all of which are herein incorporated in their entirety by reference. In addition, a universal donor cell is produced by preparing transdifferentiated cells modified so as not to express human leukocyte antigen (HLA) markers (see especially WO 95/17911).

The subject invention encompasses not only the methods described above, but also the transdifferentiated HSCs and/or MSCs produced by the methods. It also encompasses transdifferentiated HSCs that express mRNA for Isl-1, Pax-6, CK-19 and optionally insulin. It further includes the transdifferentiated MSCs that express mRNA for Isl-1, Pax-6, Glut-2, glucagon and optionally Pdx-1 and/or Pax-4.

All references cited herein are incorporated in their entirety by reference.

DETAILED DESCRIPTION OF THE INVENTION

The subject invention demonstrates for the first time the potential of non-pancreatic stem cells, and in particular, human bone marrow-derived stem cells (HSCs and MSCs) to differentiate into insulin gene expressing cells. The stem cells that are employed in the subject culture method can be any non-pancreatic stem cell, or may be limited to non-pancreatic stem cells that are not liver stem or progenitor cells (hepatoblasts or liver oval cells), or can specifically be MSCs and/or HSCs.

"Stem cell" is defined as a cell that has the capacity to both self-renew and to generate differentiated progeny. In one embodiment of the invention, non-pancreatic stem cell refers to any non-pancreatic stem cell, presently known or later discovered. In this broadest sense, non-pancreatic stem cells can include, without limitation, embryonic stem cells, adult non-pancreatic stem/progenitor cells, de-differentiated stem/progenitor cells, and multipotent adult stem cells. While stem cells have the capacity to both self-renew and to generate differentiated progeny, progenitor cells have only the capacity to generate differentiated progeny. The non-pancreatic stem cell of the subject invention is mammalian, and may or may not be human.

Embryonic stem cells have been isolated for a number of mammalian species, including human. Human embryonic stem cells are SSEA-1(−); SSEA-3(+); SSEA-4(+); TRA-1-60(+); TRA-1-81(+); and alkaline phosphatase (+). These cells can proliferate in vitro indefinitely in an undifferentiated state and are capable of differentiating into endoderm, mesoderm and ectoderm. See U.S. Pat. Nos. 6,200,806 and 5,843,780.

Adult non-pancreatic stem/progenitor cells include, without limitation, hepatic stem/progenitor cells (hepatoblasts or oval cells), mesenchymal stem/progenitor cells, neural stem/progenitor cells, adipocyte stem/progenitor cells, hematopoietic stem/progenitor cells, and skeletal muscle satellite stem/progenitor cells. As used herein "adult" stem cells refer to those tissue specific stem cells that are not embryonic, i.e., from fetal, neonatal, juvenile and adult individuals.

For example, hepatic oval cells and hepatoblasts have been described in Yin, L. et al. (1999) J. Hepatol. 31:497–507, Yin, L. et al. (2001) PAACR 42:354, and Yin, L. et al. (2001) FASEB J. Late-Breaking Abstracts:49 (LB267). The oval cells are critical in the repair of periportal liver injury. Liver hepatoblast and oval cell markers include α-fetal protein, albumin, cytokeratin 14 (CK14), c-kit, OC.2, OC.3, OC.10, OV1 and OV6. Hepatoblasts and oval cells can also express hematopoietic markers, including CD34, Thy1.1 and CD45. It is not yet known whether oval cells themselves are liver stem cells, or are progenitor cells derived from a liver stem cell or HSCs. RT-PCR investigations of liver oval cells indicate that these cells express not only insulin I and insulin II transcripts but also express RNA transcripts for transcription factors Isl1, NeuroD/β2, Nkx6.1, and Pax4. These transcription factors have important roles in regulating differentiation of pancreatic cells to endocrine cells.

MSCs are described in U.S. Pat. No. 5,486,359. Human MSCs are self-renewing and can differentiate into bone (osteoblasts), cartilage (chondrocytes) and various other types of connective tissue (adipose, muscle, tendon, ligament and dermis). MSCs available from Clonetics (Walkersville, Md.) are SH2+, SH3+, CD105+, CD166+, CD29+, CD44+, CD45− and CD34− and are obtained from bone marrow.

Fetal MSCs are described in WO 01/34775 as CD34+, CD45−, Thy-1+, AS-O2+ and SH2+ (CD105+). These cells can be used to regenerate osteoblasts, adipocytes, fibroblasts, muscle cells or cartilage.

Substantially homogeneous human HSCs are described in U.S. Pat. Nos. 5,061,620 and 5,750,397. These cells are CD34+ and Thy1+, and may be obtained from bone marrow, fetal liver, fetal and adult spleen and blood. These cells are capable of regenerating all members of the various hematopoietic (myeloid and lymphoid) lineages.

Human HSCs are also described in U.S. Pat. No. 5,840,580 as being CD34+ and CD38−, and preferably HLA-DR+. By excluding CD38+ cells, mature and progenitor cells are removed, and the selected cells are non-lineage committed with multi-lineage potential. These stem cells are capable of limited self-renewal and can differentiate into erythroid, myeloid and lymphoid progenitors and mature cells.

Human pluripotent lympho-hematopoietic stem cells are described in U.S. Pat. No. 4,714,680. These cells are My-10+ or CD34+. These cells are found in human marrow or among blood colony-forming cells and immature lymphoid precursor cells, but do not include mature human lymphoid and myeloid cells. The My-10 antigen is not lineage dependent, but appears on a variety of lympho-hematopoietic progenitor cells.

Skeletal muscle satellite cells share several characteristics of bone marrow-derived HSCs including expression of antigens Sca-1 and c-Kit, but not CD45 (Jackson K. et al. (1999) PNAS 96:14482–86)). Quiescent muscle satellite cells in vivo are CD34+, Myf5+, M-cadherin+ and MyoD−; these cells are committed to the myogenic pathway, but are arrested until injury or growth stimuli are received (Beauchamp et al. (2000) J. Cell Biol. 151:1221). There is also evidence that muscle satellite cells may replenish the hematopoietic systems of lethally irradiated recipients (Goodell et al. (2001) Ann. NY Acad. Sci. 938:18). Highly purified HSCs from bone marrow have been reported to participate in muscle regeneration; and skeletal muscle stem cells have been reported to reconstitute the hematopoietic compartment. There is also speculation that satellite cells may be derived from embryonic vasculature (Seal, P. et al. (2000) Dev. Biol. 218:115). At this time, it remains unclear whether skeletal muscle satellite cells are skeletal muscle stem or progenitor cells.

Neural crest stem cells are described in U.S. Pat. No. 5,589,376. These cells are low-affinity nerve growth factor receptor (LNGFR)+ and nestin+, are characterized by the absence of markers associated with mature peripheral nervous system neuronal and glial cells, and are capable of self-renewal and differentiation to peripheral nervous system neuronal and glial cells. Such glial cell markers include sulfatide, glial fibrillary acidic protein (GFAP) and myelin protein $P_O$, and neuronal markers include peripherin and neurofilament.

Adipose-derived stem cells are described in WO 00/53795. These cells are substantially free of adipocytes, erythrocytes and clonal populations of connective tissue stem cells. The stem cell is not defined in terms of markers, but is instead defined as being capable of achieving two or more developmental phenotypes selected from the following: adipogenic, chondrogenic, cardiogenic, dermatogenic, hematopoietic, hemangiogenic, myogenic, nephrogenic, neurogenic, neuralgiagenic, urogenitogenic, osteogenic, pericardiogenic, peritoneogenic, pleurogenic, splanchogenic, and stromal developmental phenotypes.

De-differentiated cells include stem/progenitor cells obtained by de-differentiating somatic cells. Such technique involves the injection of cell cytoplasm from a less differentiated donor cell into a recipient cell, as described in WO 01/00650. The donor cell can be an oocyte or embryonic cell. This method can result in an embryonic stem cell.

Multipotent adult stem cells (MASCs), described in WO 01/11011, can be derived from brain, liver or bone marrow, and are CD45– CD44– HLA-DR– HLAclassI-oct3/4mRNA+ and hTRT+. Using appropriate growth factors, chemokines and cytokines, MASCs can be differentiated into bone, cartilage, adipocyte, fibroblast, marrow stroma, skeletal muscle, smooth muscle, cardiac muscle, endothelial, epithelial, endocrine, exocrine, hematopoietic, glial, neuronal and oligodendrocyte cells. The MASC cells express genes (oct-4 and Rex-1) commonly found only in embryonic stem or embryonic germ cells. A full description of marker phenotype for human MASCs is provided on pages 26–27 of WO 01/11011.

In another embodiment, non-pancreatic stem cells can mean all non-pancreatic stem cells provided that the stem cells are not liver stem or progenitor cells (i.e., hepatoblasts and liver oval cells).

In another embodiment, non-pancreatic stem cells simply means HSCs and/or MSCs. Without wishing to be bound by theory, it is believed that the MSCs and HSCs are particularly amenable to transdifferentiation using the subject method because these cells continuously regenerate and replenish differentiated mesenchymal and hematopoietic populations throughout the lives of mammals. Other stem cells having similar regeneration and replenishment capacities may likewise be useful in the subject methods.

The subject invention's culture method for transdifferentiation of non-pancreatic stem cells to the pancreatic lineage preferably utilizes the culture conditions specified in Tables 1A and 1B. However, the concentrations specified in Tables 1A and 1B may be further optimized, and some components may be determined to be optional, using routine methods known in the art. Additionally, the subject invention can be practiced using medium and added factor concentrations that vary by 10–50% from those indicated in Tables 1A and 1B, without significantly impairing, and possibly improving, the outcome of the method. By using routine methods of optimization, the skilled artisan can determine an effective combination and effective concentration of the components listed in Tables 1A and 1B. In Table 1A, fetal calf serum and bovine serum albumin are specified. These components may be replaced by equivalent human serum or albumin, or fractions or specific compounds therein that permit or enhance transdifferentiation of stem cells to the pancreatic lineage.

In Table 1B, the conditioned medium of the epithelial cell lines, Capan-1, ARIP and AR42J, is preferably obtained from a confluent flask of cells cultured in 1640 medium with 10% fetal calf serum for at least one week. The FCS can be replaced by equivalent human serum or active fractions or specific compounds found therein.

The products of the subject culture method include endocrine hormones and the transdifferentiated stem cells. The endocrine hormones include insulin, somatostatin, glucagon and/or pancreatic polypeptide.

The transdifferentiated stem cells express (as mRNA and/or polypeptides) pancreatic markers including Pdx-1, Isl-1, Pax-4, Pax-6, Glut-2, CK-19, glucagon and/or insulin. Preferably, the transdifferentiated HSCs express at least Isl-1, Pax-6, CK19 and insulin. Preferably, the transdifferentiated MSCs express at least Pdx-1, Isl-1, Pax-4, Pax-6, Glut-2 and glucagon. The transdifferentiated cells vary in morphology depending on the starting stem cell. MSCs are spindle-shaped, and the transdifferentiated MSCs remain substantially spindle-shaped. Likewise, HSCs are round cells and their transdifferentiated product is also round. It may be that with continued culture and/or the addition of factors that further enhance pancreatic differentiation, that the morphology of the transdifferentiated cells will become similar to that of pancreatic progenitor or differentiated endocrine cells ($\alpha$, $\beta$, $\delta$ and PP cells).

The treatment methods of the subject invention include harvesting of endocrine hormones (especially insulin) from the cultured transdifferentiated cells, using methods known in the art, and administering the hormone to a patient. Another treatment method of the invention involves the implantation of transdifferentiated cells that produce endocrine hormones into individuals in need thereof. The subject invention provides a method of controlling or eliminating a diabetic (IDD) patient's need for insulin therapy because the transdifferentiated cells can produce insulin in vivo. Thus, the subject implantation method can be used to treat or reverse IDD. Sites of implantation include in the liver, natural pancreas, under the kidney capsule or in a subcutaneous pocket.

The appropriate cell implantation dosage in humans can be determined from existing information relating to ex vivo islet transplantation in humans, further in vitro and animal experiments, and from human clinical trials. From data relating to transplantation of ex vivo islets in humans, the number of transdifferentiated cells per patient kg can be calculated; according to the hormone production of the cells. Assuming long-term survival of the implants following transplantation (e.g., in the case of encapsulation), less than the number of $\beta$ cells in ex vivo islet transplantation may be necessary. From in vitro culture and in vivo animal experiments, the amount of hormones produced can be quantitated, and this information is also useful in calculating an appropriate dosage of implanted material. Additionally, the patient can be monitored to determine adherence to normoglycemia. If such testing indicates an insufficient response or hyperinsulinemia, additional implantations can be made or implanted material reduced accordingly.

As discussed above, it is preferred that the transdifferentiated cells be derived from the patient that is being treated so as to avoid immune rejection. However, where autologous cells are not available, it can be useful to encapsulate the transdifferentiated cells in a capsule that is permeable to the endocrine hormones, including insulin, glucagon, somatostatin and other pancreas produced factors, yet impermeable to immune humoral factors and cells. Preferably the encapsulant is hypoallergenic, is easily and stably situated in a target tissue, and provides added protection to the implanted structure.

Protection from immune rejection can also be provided by genetic modification of the transdifferentiated cells, according to any method known in the art. Autoantibody and CTL resistant cells can be produced using methods such as those disclosed in U.S. Pat. No. 5,286,632; U.S. Pat. No. 5,320,962; U.S. Pat. No. 5,342,761; and in WO 90/11354; WO 92/03917; WO 93/04169; and WO 95/17911. Alternatively, selection of resistant transdifferentiated cells (e.g., HSCs and/or MSCs) is accomplished by culturing these cells in the presence of autoantibody or IDD associated CTLs or CTLs activated with IDD specific autoantigens. As a result of these techniques, cells having increased resistance to destruction by antibody or T-lymphocyte dependent mechanisms are generated. Such cells can be implanted into an appropriate host in an appropriate tissue as disclosed herein and have increased resistance to destruction by autoimmune processes.

Likewise, the human leukocyte antigen (HLA) profile of the transdifferentiated cell (e.g., HSC or MSC) can be modified, optionally by an iterative process, in which the transdifferentiated cell is exposed to normal, allogeneic lymphocytes, and surviving cells selected. Alternatively, a site directed mutagenesis approach is used to eliminate the HLA markers from the surface of the transdifferentiated cells, and modified transdifferentiated cells thereby generated are implanted into a recipient mammal in need of such implantation.

In a specific example, the adeno-associated virus (AAV) vector system carrying the neomycin-resistance gene, neo is used. AAV can be used to transfect eukaryotic cells (Laface et al. (1988) Virology 162:483–486). In addition, the pBABE-bleo shuttle vector system carrying the phleomycin-resistance gene is used (Morgenstein et al. (1990) Nucleic Acids Res. 18:3587–3596). This shuttle vector can be used to transform human cells with useful genes as described herein.

EXAMPLE

Figure 1:
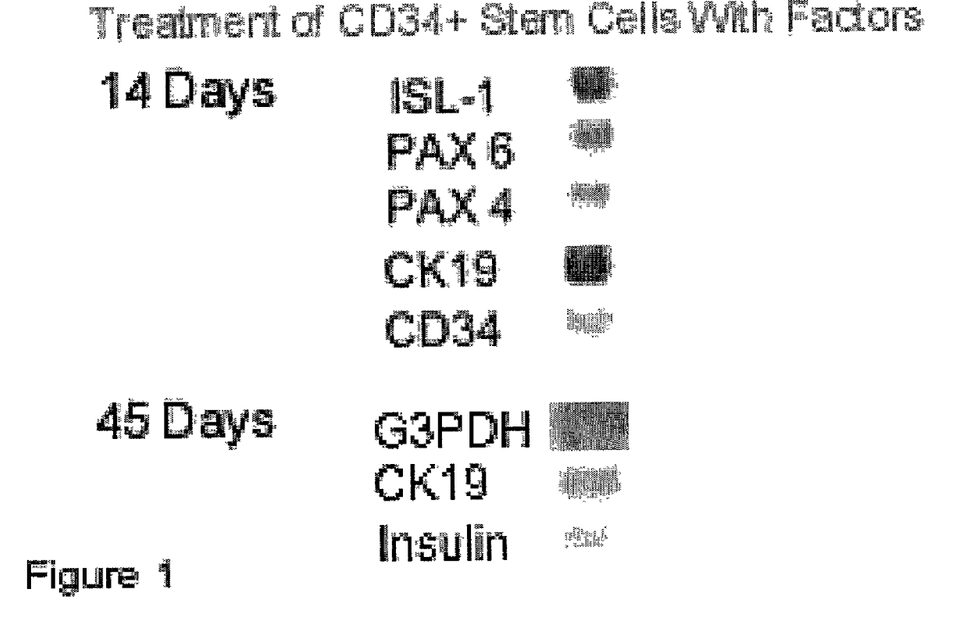
FIG. 1 illustrates the mRNAs for Isl-1, Pax-6, CK-19 and CD34 that were expressed after two weeks of culturing of HSCs in basal medium plus Table 1B factors. Continuous culture for 45 days resulted in the expression of mRNA for insulin and continued expression of CK1 9 mRNA.

Upon receipt of the HSCs, they were cultured in basal medium (Table 1A) for two days. After two days of rest, the cells were split into groups and cultured in various factors. After 14 and 45 days, RNA was extracted for RT-PCR/ Southern blot analyses to determine the expression of genes relevant to pancreas organogenesis, and not known to be involved in hematopoietic or mesenchymal pathways of differentiation. These genes include Isl-1, Pdx-1, Pax -4, Pax-6, Glut-2 and insulin. Human bone marrow-derived CD34+ stem cells treated with basal medium containing various factors (Table 1B) for 2 weeks expressed mRNAs for Isl-1, Pax-6, CK-19 along with CD34 (FIG. 1). The continuous culture of cells up to 45 days resulted in the expression of mRNA for insulin and maintenance of CK19 (FIG. 1).

Figure 2:
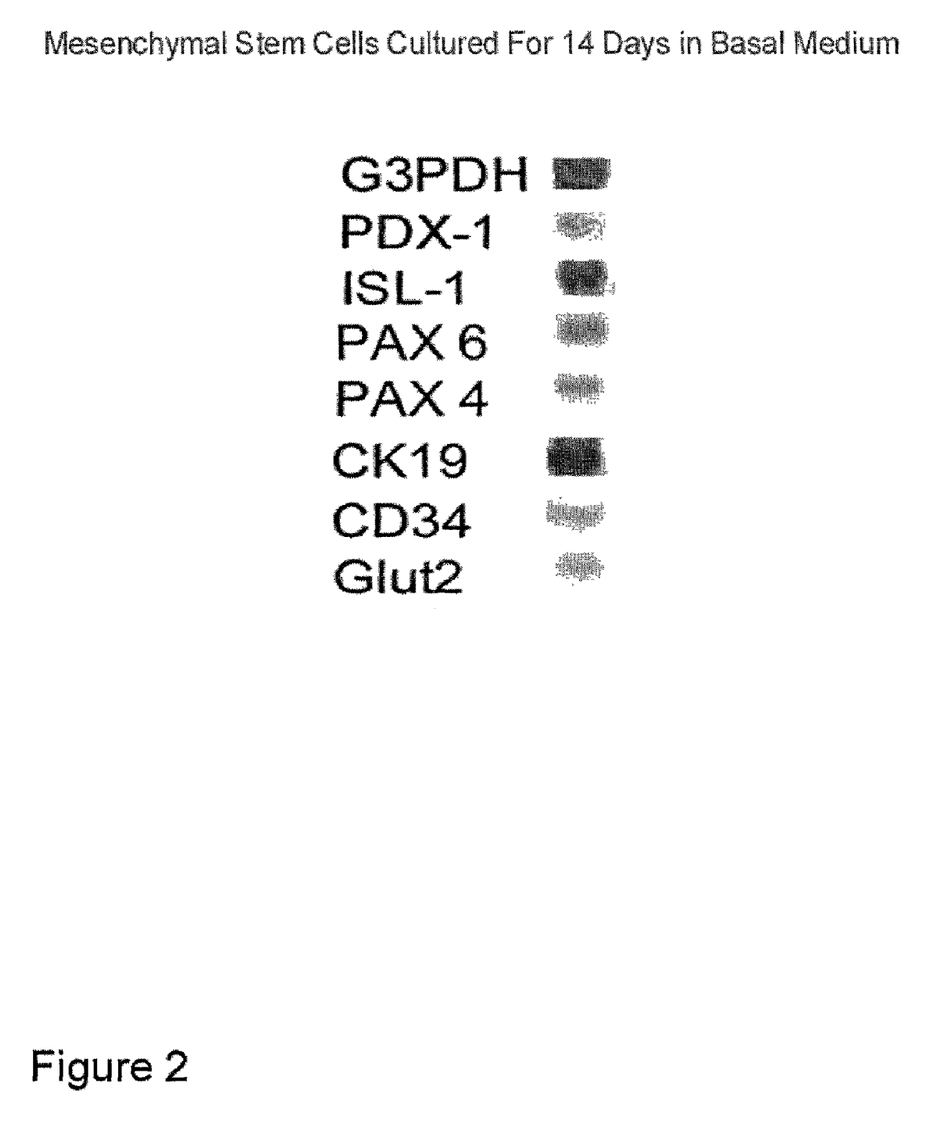
FIG. 2 illustrates the mRNAs for Pdx-1, Isl-1, Pax-4, Pax-6, Glut-2, CK-19 and CD34 that were expressed by a mixed culture of HSCs and MSCs for 14 days in basal medium alone.
Figure 3:
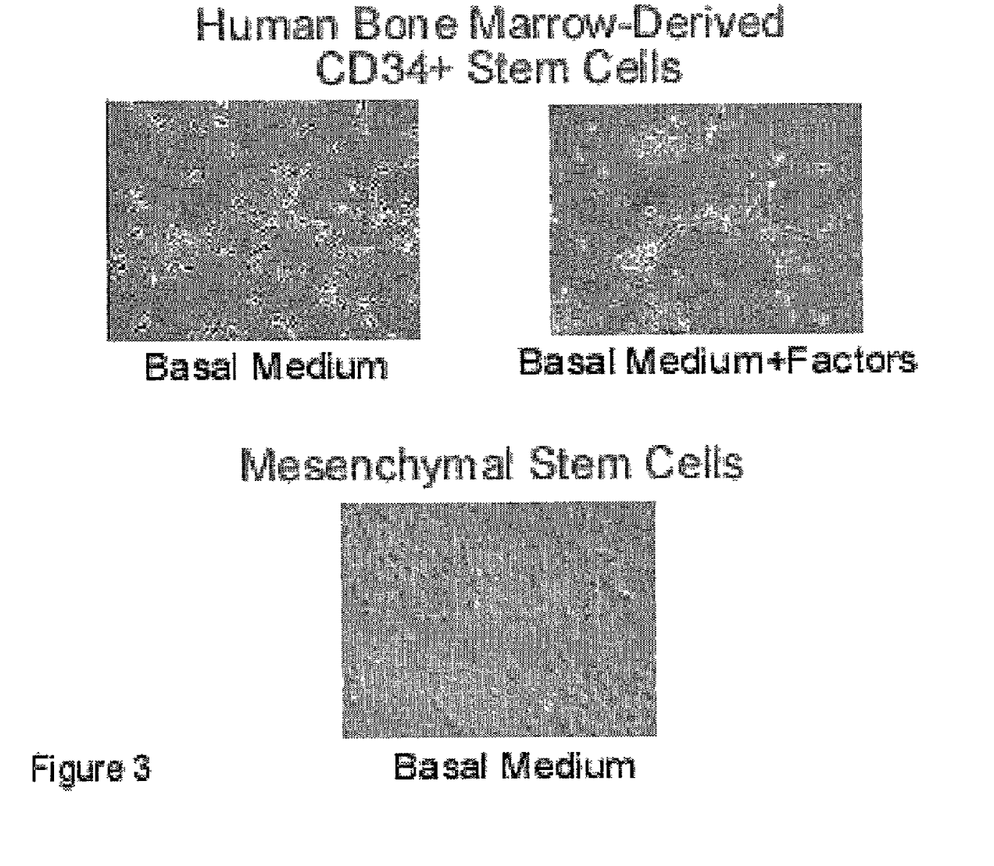
FIG. 3 shows the spherical morphology of the transdifferentiated HSCs and the spindle-shaped morphology of the transdifferentiated MSCs.

Interestingly, human bone marrow-derived CD34+ HSCs that contained MSCs as well, after 14 days of culture period in basal medium alone (Table 1A), expressed mRNAs for Pdx-1, Isl-1, Pax-4, Pax-6, Glut-2, CK-19 along with CD34 (FIG. 2). At the time of analysis, the majority of the cells were expressing typical MSC morphology (FIG. 3).

MSCs thawed immediately upon arrival and rested for 2 days in basal medium, were split into 3 groups: basal medium alone, basal medium plus factors with no conditioned medium, and basal medium with factors and conditioned medium (as set forth in Table 1B). After 21 days of culture, MSCs expressed mRNAs for Pdx-1, Isl-1, Pax-4, Pax-6, Glut-2, and glucagon along with CD34 but not for insulin (data not shown). While Isl-1 expression is seen in all 3 groups, Pdx-1 and Pax-4 appear only when factors/ conditioned medium are included. Glucagon mRNA expression is also seen even in the absence of insulin expression. The level of Glut2 mRNA expression is increased upon culturing with factors. The presence of CD34 message is interesting since undifferentiated MSCs are considered to be negative for CD34 by the cell supplier (Clonetics). At the time of analysis, a majority of the MSCs exhibited a spindle-shaped fibroblastic morphology. The HSCs exhibit both adherent and round suspension cells in the culture.

Thus, we are able to direct bone marrow-derived hematopoietic stem cells (that normally give rise to red blood cells, monocytic, granulocytic, basophilic, myeloid cells, T and B cells and platelets), and MSCs (that normally give rise to adipocytes, chondrocytes and osteocytes (Pittenger M F, et al. (1999) Science 284:143–146)) to enter into the pancreatic differentiation pathway.

TABLE 1A

Basal Medium Components

DMEM with 4500 mg/L glucose and 110 mg/L sodium pyruvate (Dulbecco's Minimal Essential Medium, Gibco-BRL)
1% bovine serum albumin (BSA)
0.1 mM 2-Mercaptoethanol
15% fetal calf serum (FCS)
Pen-Strep 1X (Gibco-BRL)
ITS (insulin, transferrin and selenium) 1X (Gibco-BRL)

TABLE 1B

Added Factors

SCF (stem cell factor) 10 ng/ml
GLP-1 (glucagon-like peptide) 10 nM
Activin A 1 nM
Betacellulin 5 nM
HGF (hepatocyte growth factor) 20 ng/ml
EGF (epidermal growth factor) 20 ng/ml
KGF (keratinocyte growth factor) 20 ng/ml
PRL (prolactin) 100 pg/ml
NGF (nerve growth factor) 3 ng/ml
TGF-alpha (transforming growth factor) 10 ng/ml
Gastrin 10 µg/ml
Conditioned medium (of Capan-1, ARIP and AR42J cell lines) 10%

It should be understood that the example and embodiments described herein are for illustrative purposes only and that various modifications or changes in light thereof will be suggested to persons skilled in the art and are to be included within the spirit and purview of this application and the scope of the appended claims.

The invention claimed is:

1. A method of transdifferentiating mammalian non-pancreatic stem cells selected from hematopoietic stem cells (HSCs) and mesenchymal stem cells (MSCs) to enter the pancreatic differentiation pathway, comprising:

culturing said stem cells in a medium that permits the expression of pancreatic differentiation markers; wherein said medium is comprised of following constituents: Dulbecco's Minimal Essential Medium (DMEM) with high glucose and sodium pyruvate, bovine or human serum albumin, 2-mercaptoethanol, fetal calf or human serum, penicillin and streptomycin (Pen-Strep), and insulin, transferrin and selenium (ITS);

wherein said HSCs are cultured for at least 14 days in said medium plus added factors comprising stem cell factor (SCF), glucagon-like peptide-1 (GLP-1), activin A, betacellulin, hepatocyte growth factor (HGF), epidermal growth factor (EGF), keratinocyte growth factor (KGF), prolactin (PRL), nerve growth factor (NGF), transforming growth factor-α (TGF-α), gastrin, and conditioned medium of a cell line selected from the group consisting of Capan-1, ARIP and AR42J;

wherein said MSCs are cultured for at least 21 days in said medium plus added factors comprising stem cell factor (SCF), glucagon-like peptide-1 (GLP-1), activin A, betacellulin, hepatocyte growth factor (HGF), epidermal growth factor (EGF), keratinocyte growth factor (KGF, prolactin (PRL), nerve growth factor (NGF), transforming growth factor-α (TGF-α), gastrin, and optionally conditioned medium of a cell line selected from the group consisting of Capan-1, ARIP and AR42J.

2. The method of claim 1 wherein the pancreatic markers that are expressed are selected from the group consisting of Pdx-1, Isl-1, Pax-4, Pax-6, Glut-2, CK-19 and insulin.

3. The method of claim 1 wherein the HSCs are CD34+.

4. The method of claim 1 wherein the MSCs are CD105+, CD166+, CD29+ and CD44+.

5. The method of claim 1 wherein the stem cells are human.

6. A method of producing an endocrine hormone comprising the method of claim 1, and further comprising the step of continuing to culture said transdifferentiated cells in said medium, whereby an endocrine hormone may be produced.

* * * * *